(12) United States Patent
Baba et al.

(10) Patent No.: US 10,524,988 B2
(45) Date of Patent: Jan. 7, 2020

(54) MEDICAL TUBE, AND MEDICAL TUBE SET

(71) Applicant: Yuzo Baba, Osaka-shi, Osaka (JP)

(72) Inventors: Yuzo Baba, Osaka (JP); Hiroyuki Nakagami, Osaka (JP)

(73) Assignee: Yuzo Baba, Osaka-shi (JP)

( * ) Notice: Subject to any disclaimer, the term of this patent is extended or adjusted under 35 U.S.C. 154(b) by 0 days.

(21) Appl. No.: 15/259,786

(22) Filed: Sep. 8, 2016

(65) Prior Publication Data

US 2017/0065492 A1 Mar. 9, 2017

(30) Foreign Application Priority Data

Sep. 8, 2015 (JP) ................................. 2015-176847

(51) Int. Cl.
*A61J 15/00* (2006.01)
*A61B 1/00* (2006.01)

(52) U.S. Cl.
CPC ....... *A61J 15/0069* (2013.01); *A61B 1/00087* (2013.01)

(58) Field of Classification Search
CPC ............... A61J 15/0007; A61J 15/0026; A61J 15/0069; A61J 15/00; A61J 15/0003; A61J 15/0015; A61J 15/003; A61J 15/0038; A61J 15/0061; A61J 15/0065; A61B 1/00087; A61B 1/0008; A61B 1/00; A61B 2017/00358; A61B 17/28; A61B 17/282; A61M 25/01; A61M 25/0105; A61M 25/0147; A61M 2025/0163; A61F 5/0076; A61F 5/0079; A61F 15/0019
See application file for complete search history.

(56) References Cited

U.S. PATENT DOCUMENTS

| | | | | |
|---|---|---|---|---|
| 4,311,148 A | * | 1/1982 | Courtney | A61M 25/02 604/175 |
| 4,769,014 A | * | 9/1988 | Russo | A61M 25/01 604/270 |
| 5,318,530 A | * | 6/1994 | Nelson, Jr. | A61J 15/00 604/103.1 |
| 5,700,287 A | * | 12/1997 | Myers | A61F 2/06 623/1.38 |
| 5,902,285 A | * | 5/1999 | Kudsk | A61J 15/0015 604/270 |
| 6,589,213 B2 | * | 7/2003 | Reydel | A61M 25/0043 600/585 |
| 7,201,738 B1 | * | 4/2007 | Bengmark | A61J 15/00 604/170.03 |
| 7,361,158 B1 | * | 4/2008 | Mooney, Jr. | A61M 25/0043 604/174 |

(Continued)

FOREIGN PATENT DOCUMENTS

JP H08-38612 A 2/1996

*Primary Examiner* — Nathan R Price
*Assistant Examiner* — Dung T Ulsh
(74) *Attorney, Agent, or Firm* — Oliff PLC

(57) ABSTRACT

An enteral nutritional supplement tube includes: a tube body; and a plurality of grasping sections. The tube body has a flexibility and is elongated. The grasping sections are disposed at a region of an outer peripheral surface of the tube body, the region being in a range from a distal end portion of the tube body to an intermediate region of the tube body in such a manner that the grasping sections are spaced apart from each other, the plurality of grasping sections being configured to be grasped.

7 Claims, 5 Drawing Sheets

(56) References Cited

U.S. PATENT DOCUMENTS

| | | | | |
|---|---|---|---|---|
| 2003/0060762 A1* | 3/2003 | Zvuloni | ................... | F25B 9/02 |
| | | | | 604/113 |
| 2003/0163100 A1* | 8/2003 | DeLegge | ............ | A61J 15/0003 |
| | | | | 604/275 |
| 2005/0049718 A1* | 3/2005 | Dann | ........................ | A61F 2/04 |
| | | | | 623/23.65 |
| 2009/0012544 A1* | 1/2009 | Thompson | .......... | A61B 17/1114 |
| | | | | 606/156 |
| 2013/0066298 A1* | 3/2013 | Deeds | ................... | A61M 39/08 |
| | | | | 604/528 |
| 2014/0276407 A1* | 9/2014 | DeVries | ........... | A61B 17/22032 |
| | | | | 604/103.08 |
| 2015/0352014 A1* | 12/2015 | Lamport | ............. | A61J 15/0003 |
| | | | | 604/528 |

* cited by examiner

MEDICAL TUBE, AND MEDICAL TUBE SET

CROSS-REFERENCE TO THE RELATED APPLICATION

This application claims priority to and the benefit of Japanese Patent Application No. 2015-176847 filed on Sep. 8, 2015, the entire disclosure of which is incorporated herein by reference.

FIELD OF THE INVENTION

The present invention relates to a medical tube and a medical tube set, which are inserted into a living body and used.

BACKGROUND ART

Medical tubes are used to directly feed a nutritional supplement or a medicine into a living body (into stomach and intestine), diagnose or sometimes treat a problematic site inside the living body (inside of the intestine) without opening abdomen.

For example, in the case of an obstruction of a small intestine (small-intestinal obstruction), if the distal end (tip end) of the medical tube can be guided to a proper position, this contributes to improvement of symptoms caused by the expansion of the intestine, and a definite diagnosis (identification of obstruction site and the cause), by reducing the internal pressure of a region of the inside of the small intestine which is more oral side than an obstruction site having been expanded due to the obstruction. By reducing the internal pressure of the intestine (intestinal tract) in this way, the obstruction is eliminated and a treatment is realized in many cases, as well as the improvement of the symptoms and the diagnosis. The medical tube used for the purpose of such a pressure-reduction treatment of the intestine is commonly inserted through a nose, and its distal end is required to be moved to a proper position in the inside of the intestine, beyond stomach and duodenum (the tube stays in the inside of the intestine for a couple of days, and therefore, the tube cannot be virtually inserted through the mouth).

In contrast, depending on the kind of the nutritional supplement or the kind of a disease, the nutritional supplement or the medicine is often required to be fed to a region of the small intestine which is more distant from the mouth than the duodenum is. In this case, typically, the nutritional supplement or the medicine continues to be fed to the region for a specified time in a particular way by use of an infusion machine. If the tube does not sufficiently reach the region of the small intestine, the nutritional supplement flows back to the inside of the stomach, which causes a risk of vomiting and aspiration. In view of this situation, the position of the distal end of the tube is important (in this case, also, the tube is inserted through the nose).

Typically, the tube can be easily inserted into the stomach in a general hospital room. However, it is not easy to insert the medical tube into the small intestine. The medical tube is moved through a narrow site at the exit of the stomach, namely, pylorus, through C-loop of the duodenum which is bent, and through a flexural area of duodenojejunal flexure, and eventually reaches the small intestine. For this reason, typically, when the tube is inserted, a patient is carried to a X-ray TV room, and the tube is inserted while seeing radioscopy by use of a contrast medium (barium obstructs (occludes) the tube and therefore cannot be used as the contrast medium in the present embodiment, and a contrast medium called Gastrografin for digestive tract, which is similar to barium and is viscosity-eliminated, is used). However, in some cases, due to the body construction or deformation of the stomach of the patient, etc., the tube cannot reach even the duodenum even under fluoroscopic guidance. The tube is pushed at the nose in the outside of the patient's body and moved into the body. The tube which is long is not tough (stiff) and a force is not well transferred to the distal end of the tube. Under this state, the tube cannot be moved smoothly. As a solution to this, it is often considered that the medical tube can be easily moved by use of an upper endoscopic instrument. For example, Japanese Laid-Open Patent Application Publication No. Hei. 8-38612 (hereinafter will be referred to as "Patent Literature 1") discloses that a ring is attached to the distal end of a medical tube and grasped by forceps, and the distal end of the tube is pulled and moved to the former half part (part closer to the mouth) of the duodenum while pulling the distal end of the tube. In this state, the ring may be released from the forceps, and the endoscopic instrument may be pulled out in a state in which the distal end of the tube is free. However, it is difficult to actually perform this. Even when the endoscopic instrument is pulled out gently, the tube and the endoscopic instrument contact each other in an adhesive state in the flexural area of the duodenum or the narrow pylorus. By pulling out the endoscopic instrument, the distal end of the tube is often moved back to the inside of the stomach together with the endoscopic instrument.

The distal end of the medical tube disclosed in Patent Literature 1 is moved through the flexural site such as the stomach and the narrow site such as the pylorus valve and reaches the obstruction site. The medical tube can be delivered (carried) by the endoscopic instrument and moved through the flexural site and the narrow site. However, at the flexural site and the narrow site, the medical tube and the endoscopic instrument contact each other in an adhesive state. Therefore, the medical tube is pulled back together with the endoscopic instrument, by pulling out the endoscopic instrument, before a treatment is performed for the obstruction site. For this reason, the distal end of the medical tube is sometimes deviated from the obstruction site after it has been delivered to the obstruction site. Thus, the distal end of the medical tube is sometimes deviated from a desired site after it has been delivered to the obstruction site, by pulling out the endoscopic instrument.

In view of the above, an object of the present invention is to provide a medical tube which is capable of surely delivering its distal end to a desired site.

SUMMARY OF THE INVENTION

A medical tube of the present invention comprises a tube body which is elongated and has a flexibility; and a plurality of grasping sections disposed at a region of an outer peripheral surface of the tube body, the region being at a distal end side of the tube body in such a manner that the plurality of grasping sections are spaced apart from each other, the plurality of grasping sections being configured to be grasped.

In accordance with the present invention, since the grasping sections are disposed at the tube body, for example, the medical tube can be moved into the living body together with an endoscopic instrument with forceps, while grasping the grasping sections by the forceps of the endoscopic instrument with forceps. In addition, since the tube body is provided with the plurality of grasping sections, the medical tube is delivered while grasping each of the plurality of grasping sections by the forceps of the endoscopic instrument with forceps, then the forceps release the grasping section, and then the endoscopic instrument with forceps is returned to a region that is closer to the proximal end of the tube body. By repeating such work, the medical tube can be inserted to a region that is more distant from the mouth in a state in which the endoscopic instrument with forceps is stopped in a specified position range. In this configuration, the medical tube can be delivered to a site that is a flexural area or is more distant from the mouth than a narrow area is, by use of the endoscopic instrument with forceps, while stopping the endoscopic instrument with forceps at a region that is closer to the proximal end than the flexure area or the narrow area is. This makes it possible to prevent a situation in which the medical tube is returned to a region that is closer to the proximal end, together with the endoscopic instrument with forceps, when the endoscopic instrument with forceps is pulled out of the living body. Thus, it becomes possible to prevent a situation in which the distal end of the medical tube is deviated from a desired site, after the medical tube has been delivered to the desired site (In other words, the medical tube can be stopped (can stay) at a region that is in the vicinity of the desired site).

A medical tube set of the present invention comprises: a tube body which is elongated and has a flexibility; and a plurality of grasping sections which are attachable to a region of an outer peripheral surface of the tube body, the region being at a distal end side of the tube body in such a manner that the plurality of grasping sections are spaced apart from each other, the plurality of grasping sections being configured to be grasped.

In accordance with this configuration, an operator or the like can dispose the plurality of grasping sections at the tube body at desired intervals. Since the plurality of grasping sections can be disposed at the tube body at desired intervals, the operator or the like can make the medical tube easily operated by the operator, and use the medical tube. Also, the medical tube provided with the plurality of grasping sections disposed at the tube body at desired intervals is used together with, for example, the forceps of the endoscopic instrument with forceps. The medical tube can be delivered to a site that is more distant from the mouth inside the living body, in a state in which the endoscopic instrument with forceps is stopped in a specified position range. Therefore, the endoscopic instrument with forceps can be stopped at a region that is closer to the mouth than the flexure area or the narrow area is. This makes it possible to prevent a situation in which the medical tube is returned to a region that is closer to the proximal end, together with the endoscopic instrument with forceps, when the endoscopic instrument with forceps is pulled out of the body. In addition, it becomes possible to prevent a situation in which the distal end of the medical tube is deviated from a desired site, after the medical tube has been moved to the desired site (In other words, the medical tube can be stopped (can stay) at a region that is in the vicinity of the desired site).

In accordance with the present invention, the distal end of the medical tube can be surely delivered to a desired site.

The above and further objects, features and advantages of the present invention will more fully be apparent from the following detailed description of preferred embodiment with reference to the accompanying drawings.

BRIEF DESCRIPTION OF THE DRAWINGS

FIG. 5(a) shows a state in which the distal end of the medical tube is delivered, and FIG. 5(b) shows a state in which the intermediate portion of the medical tube is delivered.

DETAILED DESCRIPTION OF THE PREFERRED EMBODIMENTS

Figure 1:
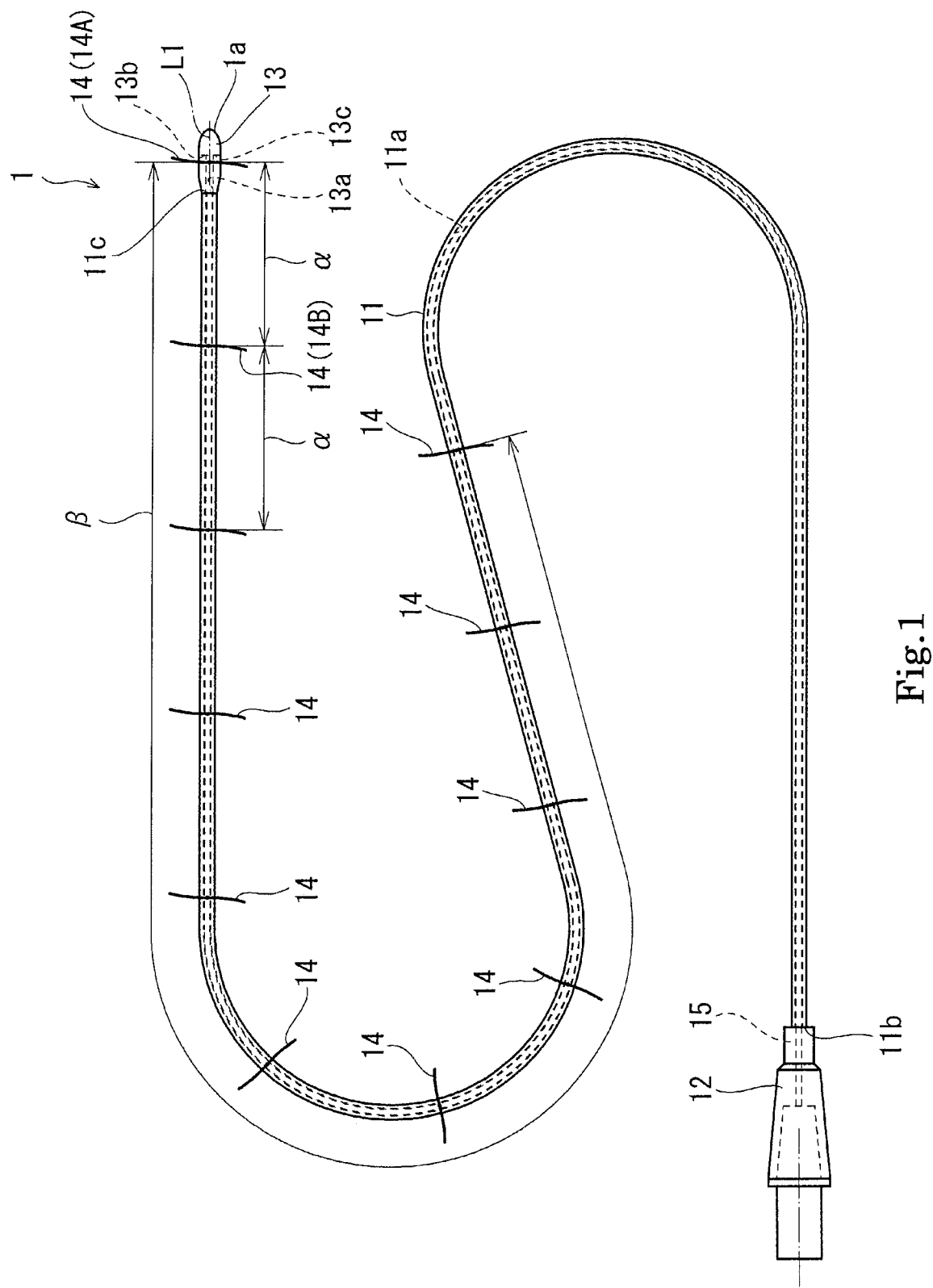
FIG. 1 is a plan view showing a medical tube according to Embodiment 1 of the present invention.

Hereinafter, an enteral nutritional supplement tube 1 of Embodiment 1 and an enteral nutritional supplement tube 1A of Embodiment 2, according to the present invention, will be described with reference to the drawings. Note that the directions stated below are defined for easier understanding of the description, and are not intended to limit the directions and the like of the constituents of the invention. The enteral nutritional supplement tube 1 and the enteral nutritional supplement tube 1A are merely the embodiments of the present invention. Therefore, the present invention is not limited to the embodiments, and can be added, deleted and modified within the scope of the invention.

Embodiment 1

[Enteral Nutritional Supplement Tube]

Medical tubes are used to directly feed a nutritional supplement or a medicine to an organ (e.g., stomach, intestine, or the like) inside a human living body or treat the organ inside the living body without opening abdomen. One example of the medical tubes which play the above roles is an enteral nutritional supplement tube 1. The enteral nutritional supplement tube 1 is used as described below. Specifically, a distal end 1a which is the tip end of the enteral nutritional supplement tube 1 is inserted into a nose, moved through throat, esophagus, and stomach, and reaches small intestine. After that, an enteral nutritional supplement is poured into a proximal end which is the base end of the enteral nutritional supplement tube 1 and is directly fed to the small intestine. The enteral nutritional supplement tube 1 used in this way includes a tube body 11, an adapter 12, a protection member 13, and a plurality of grasping strings 14.

The tube body 11 is an elongated tube having a flexibility. The tube body 11 is made of, for example, polyethylene, polypropylene, polyvinyl chloride, polyurethane, polyfluoro ethylene, polyester, polyamide, polycarbonate, ethylene vinyl acetate copolymer, ethylene acrylate copolymer, silicon rubber, or modified polymer of these. The tube body 11 has a substantially cylindrical shape, and includes a lumen 11a inside the tube body 11 to flow the enteral nutritional supplement therethrough. The adapter 12 is externally fitted and secured to a proximal end portion 11b of the tube body 11.

The adapter 12 has a substantially cylindrical shape. The tip end portion of the adapter 12 is externally fitted to a proximal end portion 11b of the tube body 11 and secured thereto. The adapter 12 has an opening 12a at a base end thereof. A connector of a tube connected to a bag or a medical bottle which contains the enteral nutritional supplement therein is connectable to the opening 12a. The enteral nutritional supplement is poured through the opening 12a. A stylet 15 is insertable into the opening 12a in a state in which the connector is not connected to the opening 12a.

The stylet 15 is a linear member made of a metal material such as a stainless steel. The stylet 15 is inserted through the opening 12a, extends through the inside of the adapter 12 and is inserted into the lumen 11a of the tube body 11. The stylet 15 inserted as described above is pushed into the tube body 11 to an extent that the distal end portion of the stylet 15 reaches a distal end portion 11c of the tube body 11. The stylet 15 extends over the entire lumen 11a. Since the stylet 15 is pushed into the tube body 11 as described above, strength of the entire tube body 11 can be increased, and the tube body 11 itself can be easily pushed into the living body. The protection member 13 is attached to the distal end portion 11c of the tube body 11.

The distal end portion of the protection member 13 has a substantially dew shape of a substantially semispherical shape. The protection member 13 includes an insertion hole 13a and a discharge passage 13b. The insertion hole 13a opens at a proximal end side and extends along its axis. The distal end portion 11c of the tube body 11 is inserted into the insertion hole 13a through the opening. In this structure, the distal end portion 11c of the tube body 11 and the distal end portion of the stylet 15 are covered and protected by the protection member 13. Therefore, it becomes possible to prevent the distal end portion 11c of the tube body 11 and the distal end portion of the stylet 15 from contacting the organ inside the living body when the enteral nutritional supplement tube 1 is inserted into the body.

The insertion hole 13a is connected at its distal end side to the discharge passage 13b. The discharge passage 13b is a passage extending in a radial direction perpendicular to the axis. The discharge passage 13b is formed with a pair of outlets 13c in a side surface of the protection member 13 and communicates with an outside region. The lumen 11a of the tube body 11 communicates with the outside region through the insertion hole 13a and the discharge passage 13b of the protection member 13. In the above-described configuration, the enteral nutritional supplement is supplied from the bag or the like to the adapter 12, flows through the lumen 11a, the insertion hole 13a, and the discharge passage 13b, and is discharged from the pair of outlets 13c provided at the distal end 1a side of the enteral nutritional supplement tube 1.

The enteral nutritional supplement tube 1 configured as described above is provided with a plurality of grasping strings 14 at specified intervals (the plurality of grasping strings 14 are disposed to be spaced apart from each other), in a range from the distal end portion 11c of the tube body 11 to the intermediate portion of the tube body 11 (to be precise, range from the protection member 13 to the intermediate portion of the protection member 13, which will be described later). The grasping strings 14 which are grasping sections can be grasped by forceps 23 which will be described later. Each of the grasping strings 14 has, for example, a thickness which is 0.1 mm or more and 1 mm or less, and a length of 10 mm or more and 50 mm or less. The grasping strings 14 are made of, for example, natural fiber (silk, cotton, etc.), a synthetic resin (polyamide, polyester, polypropylene, polyvinyl chloride, polyurethane, polycarbonate, polyfluoro ethylene, etc.), or metal (stainless steel, etc.). In the present embodiment, the grasping strings 14 are made of silk. The grasping strings 14 are made of a material which absorbs a body fluid. Thus, the grasping strings 14 contact the body fluid and are tightened inward, which makes it difficult for the grasping strings 14 to be disengaged from the tube 1. Also, the grasping strings 14 are preferably made of a material with a low friction resistance. In view of these, the grasping strings 14 are preferably made of the natural fiber (silk, cotton, etc.).

Figure 2:
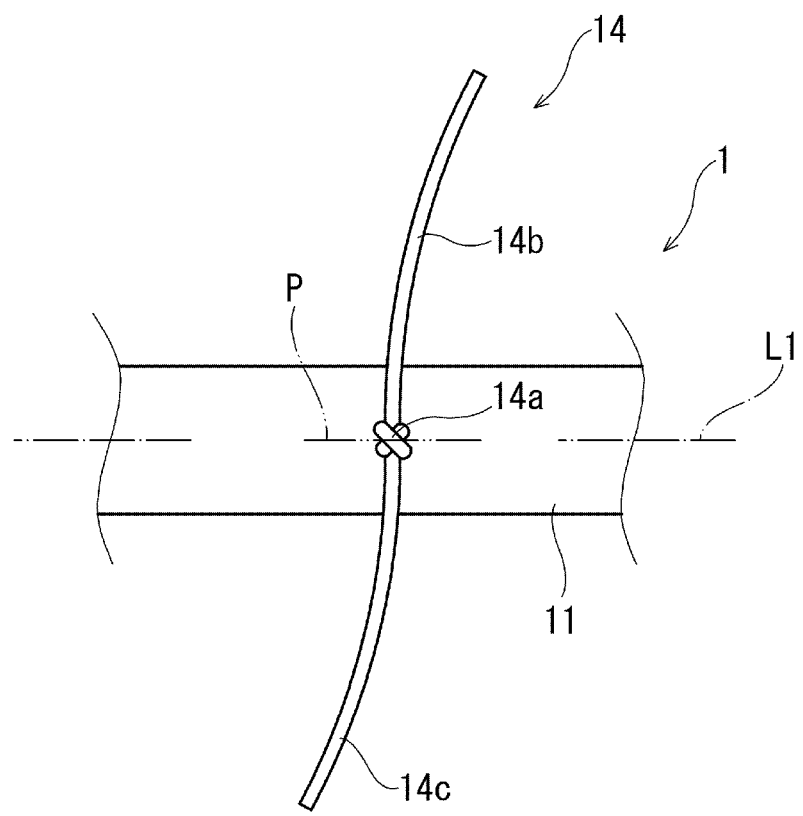
FIG. 2 is an enlarged plan view showing the medical tube of FIG. 1, in an enlarged manner.
Figure 3:
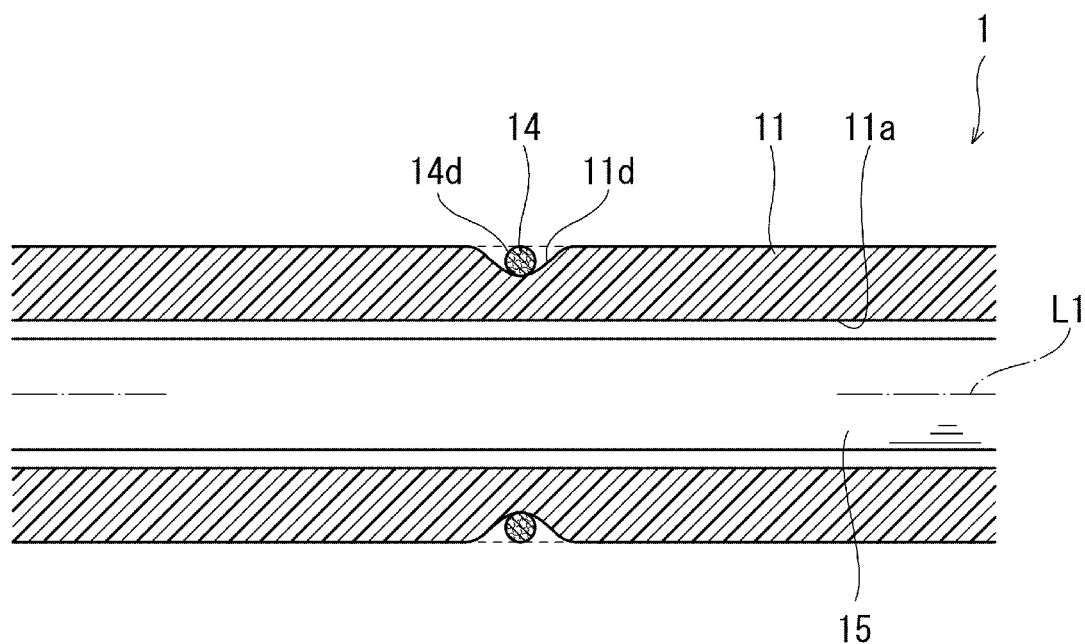
FIG. 3 is a planar cross-sectional view showing the medical tube, which is taken along a horizontal plane extending through the axis of the medical tube of FIG. 2.

As shown in FIG. 2, each of the grasping strings 14 is wound around the outer peripheral surface of the tube body 11 and tied on the outer peripheral surface. As shown in FIG. 3, the grasping string 14 is tightly wound around the tube body 11 in such a manner that a region 11d of the tube body 11 around which the grasping string 14 is wound is depressed. Thus, a wound portion 14d of the grasping string 14 which is wound around the tube body 11 is pressed against and bites into the outer peripheral surface of the tube body 11. In this way, a level difference between the wound portion 14d and the tube body 11 can be reduced. Suitably, the wound portion 14d is located to be coplanar with the outer peripheral surface of the tube body 11 (or radially inward relative to the outer peripheral surface of the tube body 11). This makes it possible to prevent a situation in which a portion protruding radially outward from the outer peripheral surface of the tube body 11 is formed on the outer peripheral surface of the tube body 11, and the tube body 11 staying inside the living body contacts a projection or the like inside the living body.

The grasping string 14 tightly wound around the outer peripheral surface of the tube body 11 in the above-described manner is firmly tied to the outer peripheral surface of the tube body 11 in a flat knot, to prevent the grasping string 14 from coming off the outer peripheral surface of the tube body 11. A knot 14a of the grasping string 14 is formed on the outer peripheral surface of the tube body 11. Since the grasping string 14 is longer than the circumferential length of the outer peripheral surface of the tube body 11, grasping portions 14b, 14c which are the both end portions of the grasping string 14 extend outward from the knot 14a. Each of the grasping portions 14b, 14c which are linear portions is linearly formed as a single line. The forceps 23 which will be described later can grasp the grasping portions 14b, 14c. Since the grasping portions 14b, 14c are tied in a flat knot, they extend to be away from a virtual plane P including an axis L1 of the tube body 11 and passing through the knot 14a. In other words, the grasping portions 14b, 14c protrude and extend laterally from the tube body 11 when viewed from above (in a plan view).

The plurality of grasping strings 14 tied in the above-described manner are disposed at intervals of α mm (suitably, $50 \leq \alpha \leq 70$), in the present embodiment, at equal intervals of 50 mm, from the distal end portion 11c of the tube body 11 to the intermediate portion of the tube body 11. The interval (spacing) a is not necessarily be an equal value in a range of 50 to 70 mm. The interval a may be longer or shorter than a value in the range of 50 to 70 mm. Further, the intervals may be different from each other. The grasping string 14 is also extended through the discharge passage 13b of the protection member 13, wound around the protection member 13, and tied to the protection member 13 in a flat knot. In brief, the grasping string 14 is also attached to the protection member 13. The grasping string 14A attached to the protection member 13 in this way is also disposed to be a α mm away from the grasping string 14B located at the most distal end side of the tube body 11. It is assumed that the distal end 1a of the enteral nutritional supplement tube 1 of the present embodiment is delivered to a site which is more distant from the mouth than a pyloric valve is. The grasping strings 14 are disposed at equal intervals, in a range from a point that is in the vicinity of the distal end 1a to a point that is (3 mm (suitably, 300≤β≤450, in the present embodiment 450 mm) away from the point that is β mm the vicinity of the distal end 1a. In a medical tube (ileus tube) in the field of a treatment of intestinal obstruction (occlusion), the grasping strings 14 are disposed at equal intervals, in a range from a point that is in the vicinity of the distal end 1a to a point that is β mm (suitably, 650≤β≤700) away from the point that is in the vicinity of the distal end 1a. In the field of enteral nutrition, regarding a patient who is old and bedridden from a disease, a reflux of food from stomach to esophagus occurs in some cases. In such a case, the distal end 1a of the tube 1 is required to be delivered to a site which is more distant from the mouth than the pyloric valve is. However, in the case of the conventional tube (the tube disclosed in the Patent Literature, the tube into which the stylet is inserted, or the tube having a weight at a tip end), it is not easy to deliver the distal end of the tube to a site which is more distant from the mouth than the pyloric valve is. On the other hand, in the invention of the present application, since the plurality of grasping strings 14 are provided in the above-described range from the point that is in the vicinity of the distal end 1a, the distal end 1a of the tube 1 can be surely delivered to a site which is more distant from the mouth than the pyloric valve is. The above-described range can be set to a suitable length, depending on a site to which the distal end 1a of the tube 1 is delivered. Further, the grasping strings 14 need not be disposed at equal intervals.

[Endoscopic Instrument with Forceps]

Figure 4:
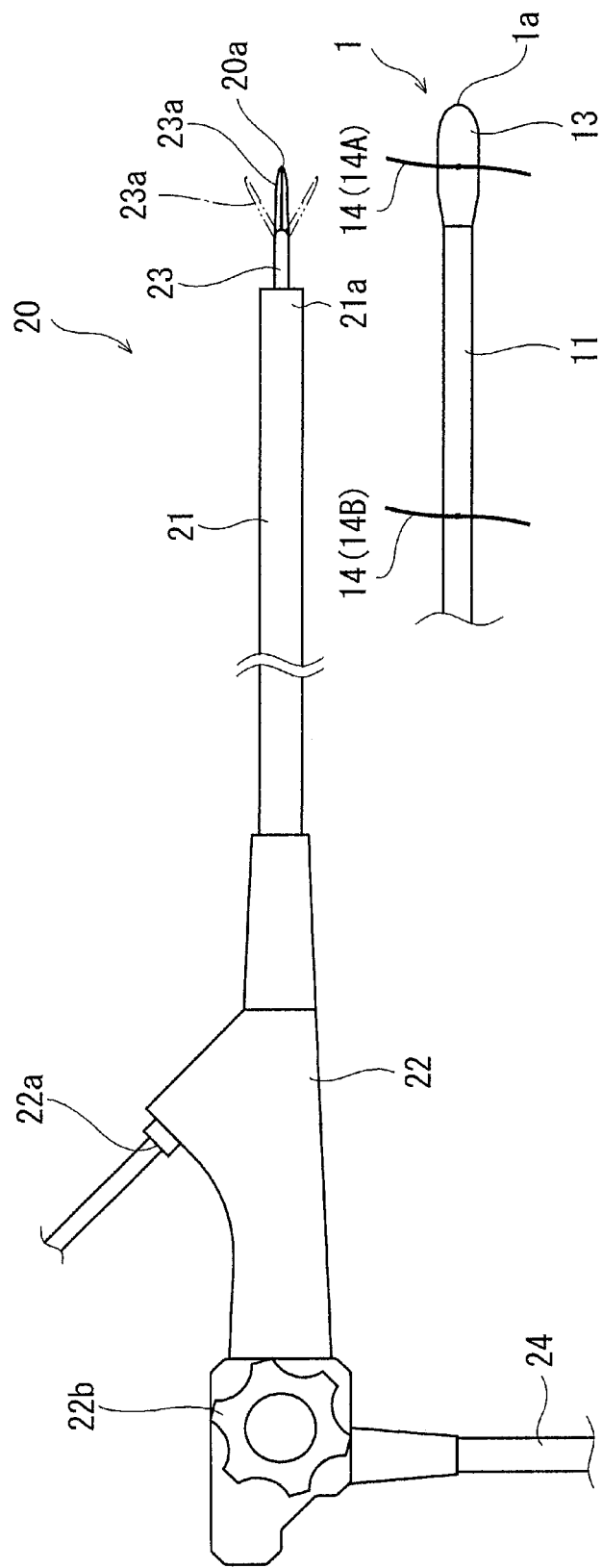
FIG. 4 is a view showing an endoscopic instrument with forceps used to deliver the medical tube into a living body.

The distal end 1a of the enteral nutritional supplement tube 1 configured as described above is inserted into a nose and delivered to the small intestine through the esophagus and the stomach, to directly feed the enteral nutritional supplement to the small intestine. However, in some cases, it is difficult to move the distal end 1a of the enteral nutritional supplement tube 1 as a single member to the small intestine, due to its low stiffness. In that case, for example, an endoscopic instrument 20 with forceps shown in FIG. 4 is used. The endoscopic instrument 20 with forceps includes an insertion section 21, a holding section 22, the forceps 23, and a cord 24. The insertion section 21 is a flexible tube and has a length for allowing the insertion section 21 inserted through the mouth or the like to be moved through the esophagus and reach the stomach and the small intestine. The insertion section 21 is thicker and is stiffer than the tube body 11 of the enteral nutritional supplement tube 1. The insertion section 21 is configured to efficiently transfer a push-in force applied to its proximal end (base end) side to its distal end (tip end) side so that the insertion section 21 is pushed and moved through the inside of the body. An imaging section and a lighting unit (not shown) are attached to a tip end portion 21a of the insertion section 21. The tip end portion 21a is configured to be bendable in all directions to orient the imaging section in various directions. The holding section 22 is provided on the other end portion of the insertion section 21.

The holding section 22 is a substantially columnar member having a taper shape. The holding section 22 is configured to be held by an operator with a hand. A forceps channel 22a is provided on the side surface of the holding section 22. The forceps 23 are inserted through the forceps channel 22a. The forceps 23 have tip end portions 23a which are openable and closable to hold an object. The base end portion of the forceps 23 is provided with an operation section (not shown) for opening and closing the tip end portions 23a. The forceps 23 configured as described above are inserted into the forceps channel 22a of the holding section 22. The insertion section 21 is provided with a forceps lumen (not shown) connected to the forceps channel 22a. The forceps 23 are inserted into the forceps lumen. The forceps lumen (not shown) opens at the tip end portion 21a of the insertion section 21. The tip end portions 23a of the forceps 23 protrude outward from the tip end portion 21a of the insertion section 21. The operation section (not shown) opens or closes the tip end portions 23a of the forceps 23 to grasp or release an object inside the living body (see two-dotted line of FIG. 4).

The insertion section 21 is provided with a plurality of lumens in addition to the forceps lumen. Among the plurality of lumens, the imaging section and the lighting unit are inserted into and attached to each of the two lumens at its tip end side. A signal line and an optical fiber are connected to the imaging section and the lighting unit. The signal line and the optical fiber are inserted through each of the lumens and extend to the holding section 22. The signal line and the optical fiber are collected together with other lines to form the cord 24. The cord 24 extends outward from the holding section 22 and is connected to a connection section (not shown). Via this connection section, the cord 24 is connected to an image processing device and a light source device. The light source device is configured to generate light. The generated light is sent to the lighting unit via the optical fiber, and the lighting unit emits the light. The image processing device is configured to perform image processing based on the signal sent from the imaging section via the signal line, and display an image taken inside the living body or the like on a monitor (not shown).

An angle operation section 22b is attached to the holding section 22. The angle operation section 22b is, for example, an operation section of a dial type. By rotating the angle operation section 22b, a drive device (not shown) is actuated to bend the tip end portion 21a of the insertion section 21. By bending the tip end portion 21a of the insertion section 21, the orientation of the lighting unit or the imaging section can be changed.

[Function of Enteral Nutritional Supplement Tube]

Hereinafter, a method (technique) for delivering the distal end 1a of the enteral nutritional supplement tube 1 to the small intestine by use of the endoscopic instrument 20 with forceps will be described. Initially, the operator inserts the distal end 1a of the enteral nutritional supplement tube 1 into the patient's nose, and also insert the endoscopic instrument 20 with forceps into the patient's mouth. The enteral nutritional supplement tube 1 and the endoscopic instrument 20 with forceps having been inserted into the nose and the mouth, respectively, are pushed toward the throat, and stopped once at the throat. Then, the operator operates the angle operation section 22b of the endoscopic instrument 20 with forceps, while seeing the monitor or the like, and causes the tip end portions 23a of the forceps 23 to face the grasping string 14A (first grasping string 14 from the distal end 1a) tied to the protection member 13 of the enteral nutritional supplement tube 1.

Figure 5A:
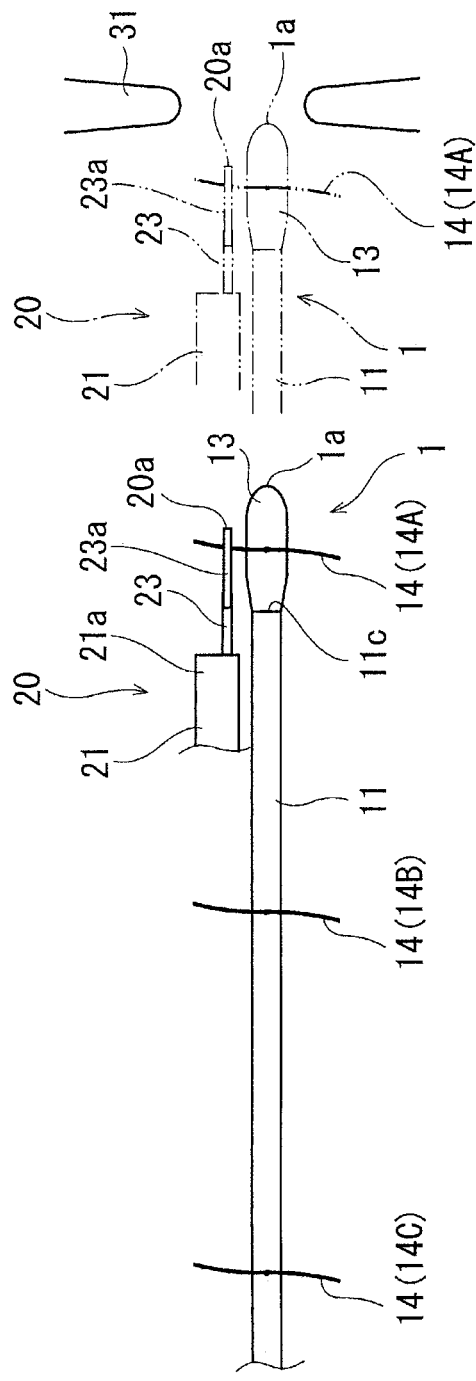
FIGS. 5(a) and 5(b) are views showing a procedure for delivering the medical tube of FIG. 1 into the living body in succession.
Figure 5B:
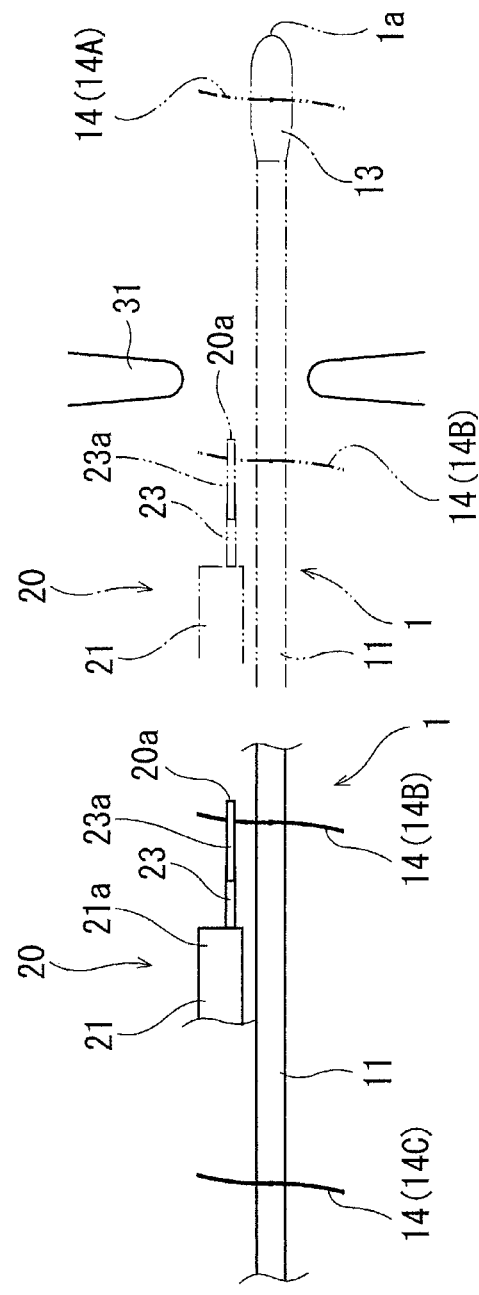

The operator operates the operation section of the forceps 23 to open or close the tip end portions 23a of the forceps 23 facing the first grasping string 14A (to be precise, the grasping portions 14b, 14c) to grasp the first grasping string 14A by the tip end portions 23a of the forceps 23. After grasping the grasping string 14A, the operator pushes in the endoscopic instrument 20 with forceps again while seeing the monitor. With this push-in operation, the distal end 1a of the enteral nutritional supplement tube 1 and the distal end 20a of the endoscopic instrument 20 with forceps are moved into the stomach through the esophagus. At a time point when the distal ends 1a, 20a reach the pyloric valve 31, the enteral nutritional supplement tube 1 and the endoscopic instrument 20 with forceps are stopped again (see FIG. 5(a)). After stopping the enteral nutritional supplement tube 1 and the endoscopic instrument 20 with forceps, the operator operates the operation section of the forceps 23 to open the tip end portions 23a of the forceps 23 to release the grasping string 14A from the forceps 23. Then, the operator pulls the endoscopic instrument 20 with forceps toward the proximal end to return the distal end 20a to a position at which the second grasping string 14B from the distal end 1a (the second grasping string 14B) can be checked (see FIG. 5(b)). Then, the operator operates the angle operation section 22b of the endoscopic instrument 20 with forceps, and causes the distal end 20a to face the second grasping string 14B. The operator operates the operation section of the forceps 23 to grasp the second grasping string 14B (to be precise, the grasping portions 14b, 14c) by the tip end portions 23a of the forceps 23.

After grasping the grasping string 14B, the operator pushes in the endoscopic instrument 20 with forceps again while seeing the monitor. Thereby, the enteral nutritional supplement tube 1 is pulled via the grasping string 14B, and the distal end 1a of the enteral nutritional supplement tube 1 is delivered through the pyloric valve 31 to a site which is more distant from the mouth than the pyloric valve 31 is. At a time point when the distal end 20a of the endoscopic instrument 20 with forceps reaches the pyloric valve 31, the operator stops the endoscopic instrument 20 with forceps again. The operator opens the tip end portions 23a of the forceps 23 again to release the grasping string 14B from the forceps 23. After releasing the grasping string 14B, the operator pulls the endoscopic instrument 20 with forceps toward the proximal end to return the distal end 20a to a position at which the third grasping string 14C from the distal end 1a (the third grasping string 14C) can be checked on the monitor. Then, the operator grasps the third grasping string 14C by the forceps 23 to deliver the enteral nutritional supplement tube 1.

As described above, in the method (technique) for delivering the enteral nutritional supplement tube 1 into the living body, the endoscopic instrument 20 with forceps is delivered while grasping the grasping string 14 with the forceps 23, then the grasping string 14 is released from the forceps 23, and then the endoscopic instrument 20 with forceps is returned, which take place in repetition. In this way, the distal end 1a of the enteral nutritional supplement tube 1 is delivered to a desired site inside the small intestine. After that, the endoscopic instrument 20 with forceps is pulled out of the mouth, and then the connector of the tube connected to the bag or the medical bottle which contains the enteral nutritional supplement therein is connected to the adapter 12 of the enteral nutritional supplement tube 1. This allows the enteral nutritional supplement to be fed to the small intestine through the enteral nutritional supplement tube 1.

As described above, the distal end 1a of the enteral nutritional supplement tube 1 can be delivered to a desired site inside the living body (to a site which is more distant from the mouth, inside the living body) while stopping the distal end 20a of the endoscopic instrument 20 with forceps at a site that is in the vicinity of the pyloric valve 31 (in the present embodiment, a site which is a little closer to the mouth than the pyloric valve 31 is (at the proximal end site). If the enteral nutritional supplement tube 1 and the endoscopic instrument 20 with forceps are inserted through a narrow region such as the pyloric valve 31, the enteral nutritional supplement tube 1 is sometimes pulled back toward the proximal end, together with the endoscopic instrument 20 with forceps, when the endoscopic instrument 20 with forceps is pulled back toward the proximal end. In contrast, in the case of the enteral nutritional supplement tube 1, the distal end 1a of the enteral nutritional supplement tube 1 can be moved to a site which is more distant from the mouth than the pyloric valve 31 is, while stopping the endoscopic instrument 20 with forceps at a site that is a little closer to the mouth than the pyloric valve 31 is. Therefore, it becomes possible to prevent a situation in which the enteral nutritional supplement tube 1 is pulled back together with the endoscopic instrument 20 with forceps, when the endoscopic instrument 20 with forceps is pulled out. This allows the distal end 1a of the enteral nutritional supplement tube 1 to stay at a region that is vicinity of the desired site, after the distal end 1a of the enteral nutritional supplement tube 1 has been delivered to the desired site. In the present medical tube, the tip ends of the holding forceps are exposed from a forceps opening at the tip end of the upper endoscopic instrument (gastric camera), and the grasping section attached to the medical tube is grasped. In this state, the medical tube is moved into the duodenum and thereby the distal end of the medical tube can be moved to a proper site. Normally, this can be performed in a hospital ward, and X-ray fluoroscopy becomes unnecessary. After the medical tube is inserted into the body, only an abdominal X-ray is to be taken to check the position of the distal end of the medical tube.

In the enteral nutritional supplement tube 1, the forceps 23 can grasp the grasping portions 14b, 14c of the grasping string 14. Therefore, it is not necessary to manufacture a new instrument used exclusively for delivering the enteral nutritional supplement tube 1. Thus, the enteral nutritional supplement tube 1 has a versatility. The enteral nutritional supplement tube 1 includes the grasping portions 14b, 14c of the grasping string 14 to be grasped by the forceps 23. Therefore, the tube body 11 need not be grasped by the forceps 23 and is not damaged. Further, in the enteral nutritional supplement tube 1, the grasping string 14 is tied to the tube body 11 in a flat knot, and thereby the grasping portions 14b, 14c of the grasping string 14 protrude laterally from the tube body 11, without extending along the tube body 11. The grasping portions 14b, 14c of the grasping string 14 can be easily formed by merely tying the grasping string 14 to the tube body 11 in a flat knot. The grasping portions 14b, 14c of the grasping string 14 protrude laterally from the tube body 11. This makes it possible to prevent the tube body 11 from interfering with the tip end portions 23a of the forceps 23 when the grasping portions 14b, 14c of the grasping string 14 are grasped by the tip end portions 23a. Therefore, the forceps 23 can easily grasp the grasping portions 14b, 14c of the grasping string 14.

Although the grasping portions 14b, 14c of the grasping string 14 of the enteral nutritional supplement tube 1 have a linear shape, they may have an annular shape instead of the linear shape. However, if the grasping portions 14b, 14c of the grasping string 14 are formed to have the annular shape, the tip end portions 23a of the forceps 23 interfere with and are engaged with the grasping portions 14b, 14c. For this reason, when the forceps 23 are pulled back, the tip end portions 23a of the forceps 23 are engaged with the grasping portions 14b, 14c, and thereby the enteral nutritional supplement tube 1 is sometimes pulled back together with the endoscopic instrument 20 with forceps. In contrast, in a case where the grasping portions 14b, 14c have the linear shape, the tip end portions 23a of the forceps 23 and the grasping portions 14b, 14c are not easily engaged with each other even when the tip end portions 23a of the forceps 23 interfere with the grasping portions 14b, 14c. In addition, the tip end portions 23a of the forceps 23 and the grasping portions 14b, 14c are easily disengaged from each other even when they are engaged with each other. Therefore, it becomes possible to prevent a situation in which the enteral nutritional supplement tube 1 is pulled back together with the endoscopic instrument 20 with forceps, when the forceps 23 are pulled back and the tip end portions 23a of the forceps 23 interfere with the grasping portions 14b, 14c.

In a case where the grasping portions 14b, 14c have the annular shape, the grasping portions 14b, 14c may get wet due to a gastric fluid or the like and adhere to the tube body 11. Due to the adhesion to the tube body 11, the forceps 23 cannot grasp the grasping portions 14b, 14c. In contrast, the grasping portions 14b, 14c of the grasping string 14 of the enteral nutritional supplement tube 1 have the linear shape, and protrude laterally from the tube body 11. Therefore, the grasping portions 14b, 14c do not easily adhere to the tube body 11. Further, if the grasping portion 14b of the two grasping portions 14b, 14c of the grasping string 14 adheres to the tube body 11, the forceps 23 can grasp the grasping portion 14c. Further, even if both of the grasping portions 14b, 14c of one of the grasping strings 14 adhere to the tube body 11, the enteral nutritional supplement tube 1 can be delivered by grasping the grasping portions 14b, 14c of any one of the remaining grasping strings 14 disposed at the tube body 11.

In the above-described embodiment, the plurality of grasping strings 14 are tied to the tube body 11 of the enteral nutritional supplement tube 1. Hereinafter, an enteral nutritional supplement tube set in which the plurality of grasping strings 14 are not tied to the tube body 11 will be described. In the enteral nutritional supplement tube set, the operator or the like needs to tie the plurality of grasping strings 14 to the tube body 11 before the operator or the like performs a manual operation. The plurality of grasping strings 14 can be disposed at the tube body 11 at intervals as desired by the operator. In other words, the operator or the like can make the enteral nutritional supplement tube 1 easily operated by the operator, and use the enteral nutritional supplement tube 1. In the case of the enteral nutritional supplement tube set, it is desired that the intervals at which the plurality of grasping strings 14 are disposed at the tube body 11 can be easily seen. For example, scale marks indicating a distance from the distal end of the tube body 11 are formed on the outer peripheral surface of the tube body 11.

Embodiment 2

The enteral nutritional supplement tube 1A according to Embodiment 2 is similar in configuration to the enteral nutritional supplement tube 1 according to Embodiment 1. Hereinafter, regarding the configuration of the enteral nutritional supplement tube 1A according to Embodiment 2, differences from the enteral nutritional supplement tube 1 according to Embodiment 1 will be mainly described. The same constituents as those of the enteral nutritional supplement tube 1 according to Embodiment 1 are designated by the same reference symbols and will not be described repeatedly.

Figure 6:
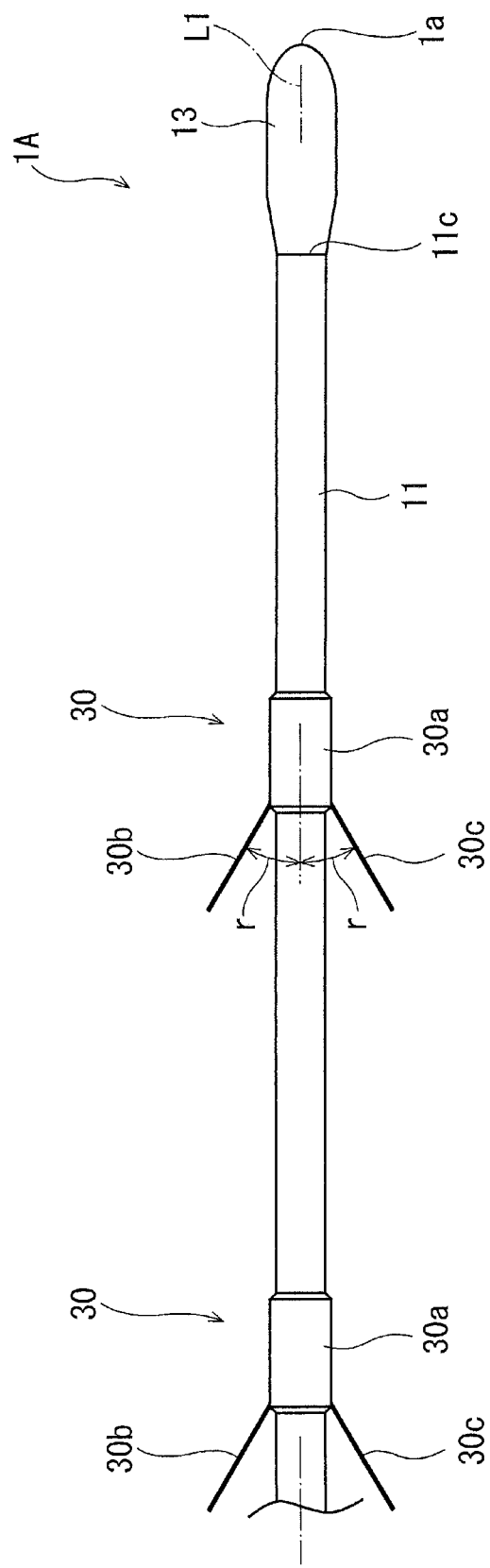
FIG. 6 is an enlarged plan view showing a medical tube according to Embodiment 2 of the present invention.

As shown in FIG. 6, the enteral nutritional supplement tube 1A includes a plurality of grasping rings 30 instead of the plurality of grasping strings 14. Each of the plurality of grasping rings 30 which are the grasping sections includes a body portion 30a, and two grasping portions 30b, 30c. The body portion 30a has a substantially cylindrical shape. The inner diameter of the body portion 30a is substantially equal to the outer diameter of the tube body 11. The body portion 30a is made of a synthetic resin such as polyethylene, polypropylene, or the like, or a metal such as a stainless steel. The body portion 30a is secured to the tube body 11 by caulking, fusion boding, or fitting, in a state in which the body portion 30a is externally disposed at the tube body 11. The axial end portions of the body portion 30a have a taper shape, which reduces or eliminates a level difference between the body portion 30a and the tube body 11. In this configuration, it becomes possible to prevent a situation in which a portion with a level difference contacts a projection or the like inside the living body. Further, the two grasping portions 30b, 30c are integrally provided on a region of the body portion 30a that is in the vicinity of the end portion of the body portion 30a which is closer to the proximal end.

The two grasping portions 30b, 30c are protruding members having a substantially linear shape, and can be grasped by the tip end portions 23a of the forceps 23, as in the case of the grasping portions 14b, 14c of the grasping string 14 according to Embodiment 1. When viewed from above (in a plan view), the two grasping portions 30b, 30c are disposed to be symmetric with respect to the axis of the body portion 30a (namely, the axis L1 of the tube body 11). The two grasping portions 30b, 30c are disposed to form a predetermined angle γ (30 degrees≤γ≤90 degrees) with respect to the axis of the body portion 30a. The predetermined angle γ is preferably 90 degrees or less, and may be less than 30 degrees. This allows the two grasping portions 30b, 30c to play the same role as that of the grasping portions 14b, 14c. The plurality of grasping rings 30 are disposed at intervals of a in a range from the distal end portion 11c of the tube body 11 to the intermediate portion of the tube body 11, and function as in the grasping strings 14 of Embodiment 1.

The enteral nutritional supplement tube 1A configured as described above is capable of delivering the distal end 1a of the enteral nutritional supplement tube 1A to the small intestine by use of the endoscopic instrument 20 with forceps, as in the case of the enteral nutritional supplement tube 1 according to Embodiment 1. The enteral nutritional supplement tube 1A can obtain the same advantages as those of the enteral nutritional supplement tube 1 according to Embodiment 1. To allow the operator to make the enteral nutritional supplement tube 1 easily operated and use it, it is preferable that the plurality of grasping rings 30 are fittable to the tube body 11 by the operator.

Other Embodiments

Although in the enteral nutritional supplement tubes 1, 1A of the above-described embodiments, the grasping strings 14 and the grasping rings 30 are separate from the tube body 11, they may be integrated with the tube body 11. For example, the tube body 11 can be formed to have concave/convex portions on the outer peripheral surface thereof by changing an extrusion speed when the tube body 11 is formed by extrusion (in this case, the convex portions are the grasping portions). The forceps 23 may directly grasp the convex portions to deliver the enteral nutritional supplement tube. Although in the enteral nutritional supplement tube 1, the grasping strings 14 are tied and attached to the tube body 11, the grasping strings 14 may be attached to the tube body 11 by means of an adhesive or fusion bonding. Although in the enteral nutritional supplement tube 1A, each of the plurality of grasping rings 30 includes the grasping portions 30b, 30c, the grasping portions 30b, 30c may be omitted. In this case, the forceps 23 may directly grasp the body portion 30a of the grasping ring 30. To allow the forceps 23 to easily grasp the body portion 30a of the grasping ring 30, a grasping ring may be formed of an elastic material or the outer peripheral surface of the grasping ring 30 may be formed with an annular recess. Although in Embodiment 1 and Embodiment 2, the enteral nutritional supplement tube 1, 1A for feeding the enteral nutritional supplement to the small intestine has been exemplarily described as an example of the medical tube, the medical tube is not limited to the enteral nutritional supplement tube 1, 1A. For example, the medical tube may be a balloon catheter for expanding the obstruction site formed on a digestive organ such as the duodenum, the small intestine, or the large intestine. For example, the enteral nutritional supplement tube 1, 1A may be used as an ileus tube used for treatment of the intestine obstruction. Further, the site into which the medical tube is to be inserted is not limited to the nose and may be the mouth, or a hole of the throat formed by cutting. Or, the medical tube may be inserted into a hole formed by opening the abdomen. Thus, the site into which the medical tube is to be inserted is not limited.

Although in the above-described method (technique) for delivering the enteral nutritional supplement tube 1, 1A, the enteral nutritional supplement tube 1, 1A is delivered while stopping the distal end 20a of the endoscopic instrument 20 with forceps at the site which is a little closer to the mouth than the pyloric valve 31 is, it is not always necessary to stop the distal end 20a at the site which is a little closer to the mouth than the pyloric valve 31 is. Instead, the distal end 20a may be moved to a site which is a little more distant from the mouth than the pyloric valve 31 is. Even in this case, the enteral nutritional supplement tube 1, 1A is pulled back for only a small distance when the endoscopic instrument 20 with forceps is pulled back. Therefore, the distal end 1a of the enteral nutritional supplement tube 1, 1A can be stopped at a region which is in the vicinity of the predetermined site.

In the above-described method (technique) for delivering the enteral nutritional supplement tube 1, 1A, the distal end 1a of the enteral nutritional supplement tube 1, 1A is delivered to the site which is more distant from the mouth than the pyloric valve 31 is. Moreover, the structure of the enteral nutritional supplement tube 1, 1A is useful in moving the enteral nutritional supplement tube 1, 1A to a flexural site such as the small intestine, or the like, as well as the narrow site such as the pyloric valve 31. Specifically, the distal end 1a of the enteral nutritional supplement tube 1, 1A may be delivered to the small intestine, or the like while stopping the distal end 20a of the endoscopic instrument 20 with forceps at the site which is a little closer to the mouth than the small intestine is. In this way, the same advantages as those of the above-described method (technique) can be achieved.

Since the grasping portions 30b, 30c are disposed at a predetermined angle γ of 90 degrees or less with respect to the axis of the body portion 30a, catheter can be inserted with a low resistance. Further, since the grasping portions 30b, 30c are disposed at a predetermined angle γ of 30 degrees or more with respect to the axis of the body portion 30a, the forceps 23 may easily grasp the grasping portions 30b, 30c.

Numerous improvements and alternative embodiment of the invention will be apparent to those skilled in the art in view of the foregoing description. Accordingly, the description is to be construed as illustrative only, and is provided for the purpose of teaching those skilled in the art the best mode of carrying out the invention. The details of the structure and/or function may be varied substantially without departing from the spirit of the invention.

What is claimed is:

1. A medical tube comprising:
   a tube body which is elongated and has a flexibility; and
   a plurality of grasping sections disposed at a region of an outer peripheral surface of the tube body, the region being at a distal end side of the tube body in such a manner that locations where the plurality of grasping sections are attached to the outer peripheral surface of the tube body are spaced apart from each other in a lengthwise direction of the tube body, the plurality of grasping sections being configured to be grasped,
   wherein each of the plurality of grasping sections includes a grasping portion configured to be grasped by forceps, the grasping portion being a string made of fiber and having a thickness of 0.1 mm or more and 1 mm or less and a length of 10 mm or more and 50 mm or less,
   wherein the grasping portion has a shape in which a tip end portion of the grasping portion in a lengthwise direction of the grasping portion protrudes laterally and extends away from the tube body, with respect to a base end portion of the linear grasping portion in the lengthwise direction of the grasping portion, and
   wherein the grasping portion is grasped by the forceps and delivered inside a digestive organ to allow the tube body to be delivered to a site which is more distant from a mouth.

2. The medical tube according to claim 1,
   wherein each of the plurality of grasping sections is attached to the tube body in such a manner that each of the plurality of grasping sections is wound around the tube body, and the region of the outer peripheral surface of the tube body around which each of the plurality of grasping sections is wound is depressed inward.

3. A medical tube comprising:
   a tube body which is elongated and has a flexibility; and
   a plurality of grasping sections disposed at a region of an outer peripheral surface of the tube body, the region being at a distal end side of the tube body in such a manner that locations where the plurality of grasping sections are attached to the outer peripheral surface of the tube body are spaced apart from each other in a lengthwise direction of the tube body,
   wherein each of the plurality of grasping sections includes a ring portion which is separate from the tube body and is secured to the outer peripheral surface of the tube body, and a linear grasping portion configured to be grasped by forceps, the grasping portion being a string made of fiber and having a thickness of 0.1 mm or more and 1 mm or less and a length of 10 mm or more and 50 mm or less,
   wherein the grasping portion has a shape in which a tip end portion of the grasping portion in a lengthwise direction of the grasping portion protrudes laterally and extends away from the tube body, with respect to a base end portion of the grasping portion in the lengthwise direction of the grasping portion, and
   wherein the grasping portion is grasped by the forceps and delivered inside a digestive organ to allow the tube body to be delivered to a site which is more distant from a mouth.

4. A medical tube set comprising:
   a tube body which is elongated and has a flexibility; and
   a plurality of grasping sections which are attachable to a region of an outer peripheral surface of the tube body, the region being at a distal end side of the tube body in such a manner that locations where the plurality of grasping sections are attached to the outer peripheral surface of the tube body are spaced apart from each other in a lengthwise direction of the tube body, the plurality of grasping sections being configured to be grasped, wherein each of the plurality of grasping sections includes a grasping portion configured to be grasped by forceps, the grasping portion being a string made of fiber and having a thickness of 0.1 mm or more and 1 mm or less and a length of 10 mm or more and 50 mm or less, wherein the grasping portion has a shape in which a tip end portion of the grasping portion in a lengthwise direction of the grasping portion protrudes laterally and extends away from the tube body, with respect to a base end portion of the grasping portion in the lengthwise direction of the grasping portion, and wherein the grasping portion is grasped by the forceps and delivered inside a digestive organ to allow the tube body to be delivered to a site which is more distant from a mouth.

5. The medical tube according to claim 1, wherein the plurality of grasping sections includes at least three grasping sections that are disposed in a range from a point of the distal end of the tube body to a point which is 450 mm away from the distal end of the tube body.

6. The medical tube according to claim 3, wherein the plurality of grasping sections includes at least three grasping sections that are disposed in a range from a point of the distal end of the tube body to a point which is 450 mm away from the distal end of the tube body.

7. The medical tube set according to claim 4, wherein the plurality of grasping sections includes at least three grasping sections that are disposed in a range from a point of the distal end of the tube body to a point which is 450 mm away from the distal end of the tube body.

* * * * *